United States Patent
Dragan et al.

(10) Patent No.: US 6,422,866 B2
(45) Date of Patent: Jul. 23, 2002

(54) DENTAL CAPSULE OR CARTRIDGE WITH FRANGIBLE END SEAL

(75) Inventors: William B. Dragan, Easton; Gordon Rowe, Wallingford, both of CT (US)

(73) Assignee: Centrix, Inc., Shelton, CT (US)

(*) Notice: Subject to any disclaimer, the term of this patent is extended or adjusted under 35 U.S.C. 154(b) by 0 days.

(21) Appl. No.: 09/801,381

(22) Filed: Mar. 7, 2001

Related U.S. Application Data

(63) Continuation of application No. 09/188,658, filed on Nov. 9, 1998, now abandoned, which is a continuation-in-part of application No. 08/982,951, filed on Dec. 2, 1997, now Pat. No. 6,135,771.

(51) Int. Cl.$^7$ .............................. A61C 5/04; B65D 25/08
(52) U.S. Cl. ....................... 433/90; 604/200; 215/252; 222/541.6
(58) Field of Search ................................. 604/200, 201, 604/206, 241; 433/89, 90; 215/50, 252; 222/541.5, 541.6

(56) References Cited

U.S. PATENT DOCUMENTS

| | | | | |
|---|---|---|---|---|
| 3,581,399 A | * | 6/1971 | Dragan | |
| 3,858,739 A | * | 1/1975 | Turner et al. | |
| 3,900,954 A | * | 8/1975 | Dragan | |
| 4,198,756 A | * | 4/1980 | Dragan | |
| 4,330,280 A | * | 5/1982 | Dougherty et al. | |
| 4,410,096 A | * | 10/1983 | Paradis | 215/50 |
| 4,415,094 A | * | 11/1983 | Bavnsfelt | 215/252 |
| 4,512,475 A | * | 4/1985 | Federighi | 215/50 |
| 4,546,893 A | * | 10/1985 | Stull | 215/252 |
| 5,172,807 A | * | 12/1992 | Dragan et al. | 433/90 |
| 5,640,998 A | * | 6/1997 | Schneider et al. | 215/252 |
| 5,897,009 A | * | 4/1999 | O'Meara | 215/50 |
| 6,135,771 A | * | 10/2000 | Dragan et al. | 433/90 |

* cited by examiner

Primary Examiner—Ralph A. Lewis
(74) Attorney, Agent, or Firm—Fattibene & Fattibene; Paul A. Fattibene; Arthur T. Fattibene

(57) ABSTRACT

A dental capsule or cartridge for packing, storing and dispensing a dental filling material and the like having a body portion for containing a predetermined amount of dental material having a discharge nozzle connected at one end of the body portion and having the other end opened and sealable by a displaceable piston. A sealing cap is integrally formed at the discharge end of the discharge nozzle and is connected thereto by a frangible or weakened portion whereby upon the application of a breaking force, the sealing cap is readily separated from the discharge end of the nozzle to expose or form the discharge orifice. The sealing cap may also be provided on one end thereof with a cavity or sealing spike by which the discharge orifice may be resealed, if desired. A vent is also provided adjacent the open end of the capsule to facilitate the filling of the capsule, and which is sealed by the seating of the displaceable piston in the open end.

3 Claims, 2 Drawing Sheets

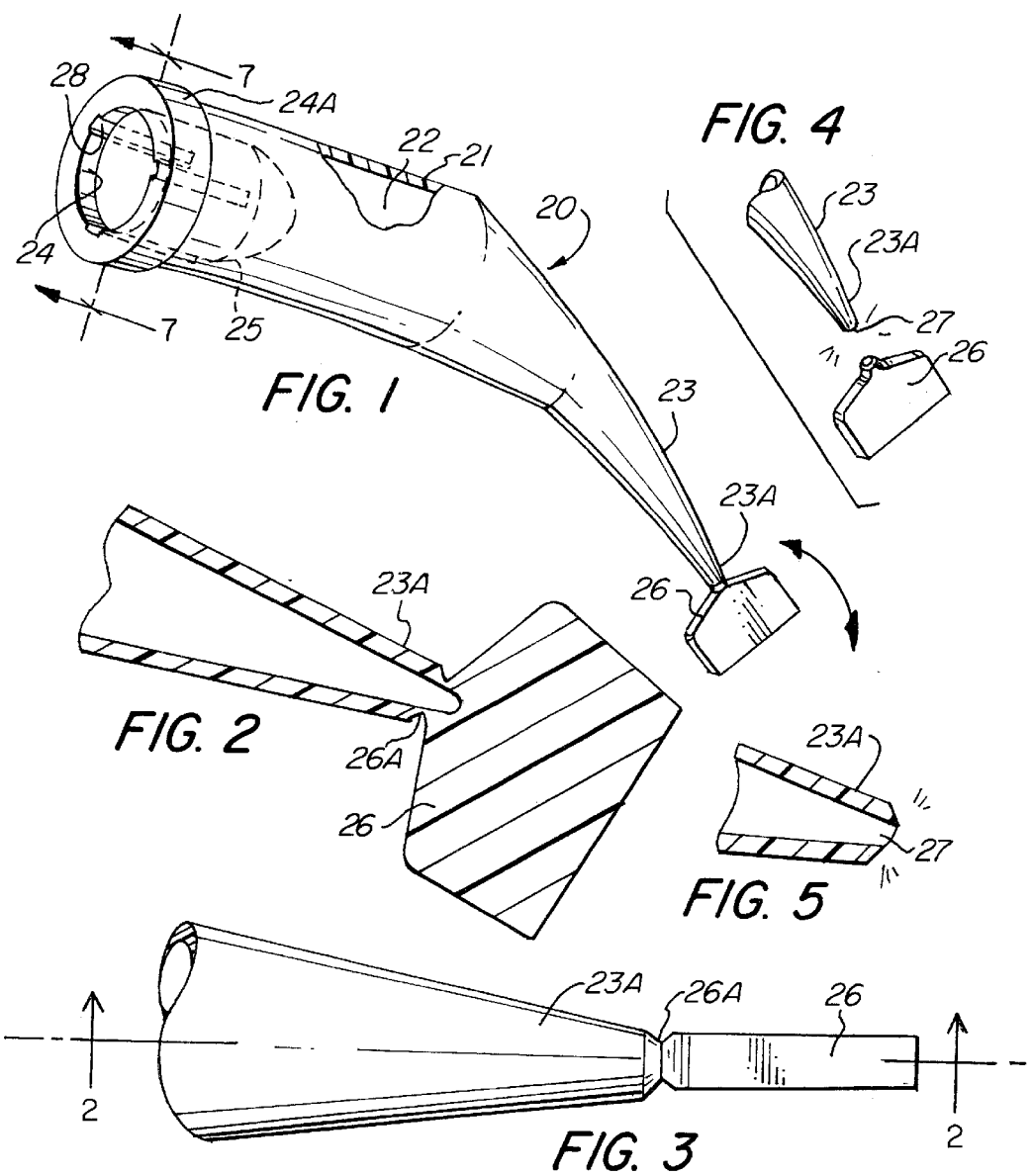
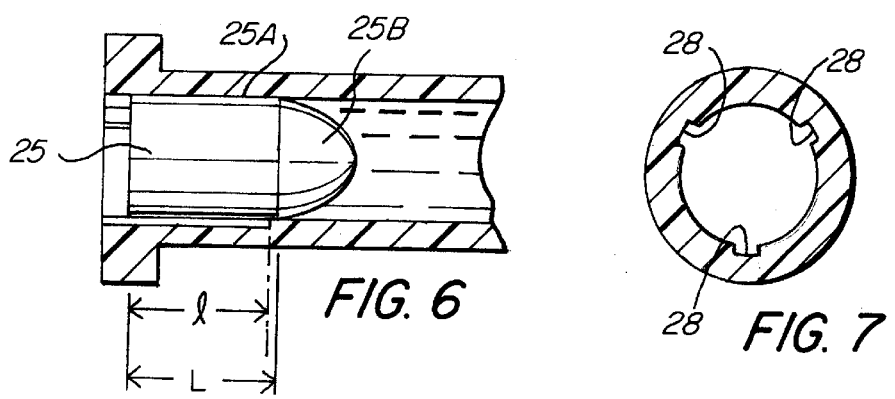

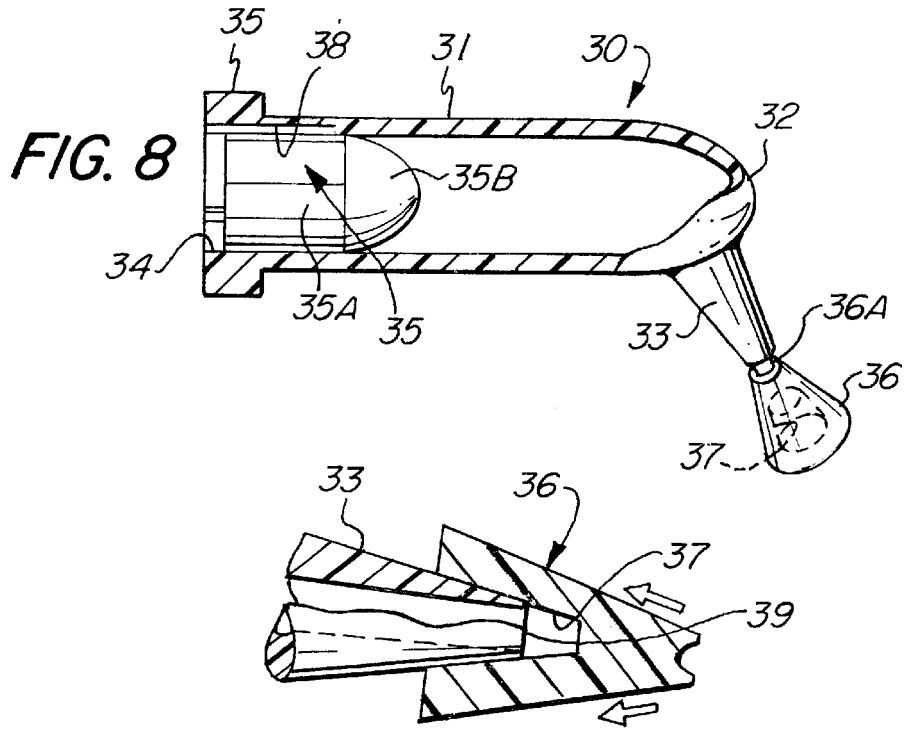
FIG. 8
FIG. 9
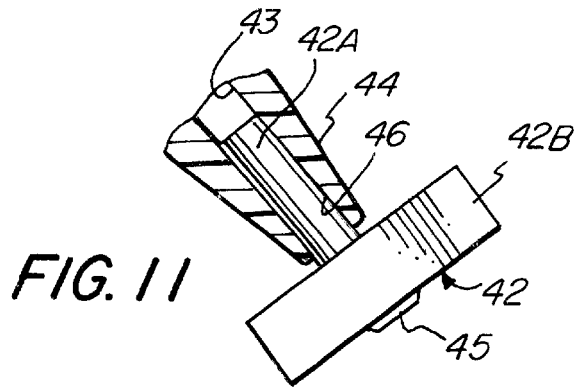
FIG. 11
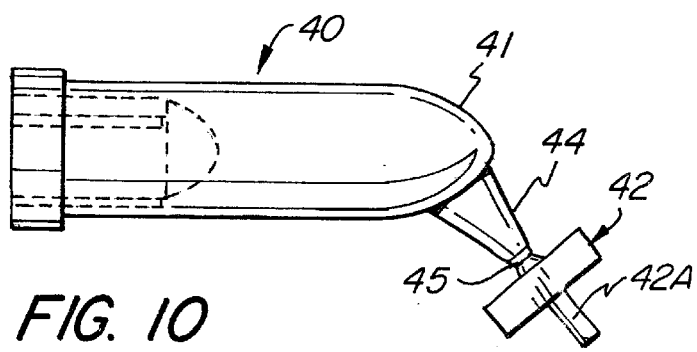
FIG. 10

DENTAL CAPSULE OR CARTRIDGE WITH FRANGIBLE END SEAL

RELATED APPLICATIONS

This application is a continuation application of patent application Ser. No. 09/188,658 filed Nov. 9, 1998 for Dental Capsule Or Cartridge With Frangible End Seal (now abandoned), which is a continuation-in-part application of patent application Ser. No. 08/982,951 filed Dec. 02, 1997 for Dental Cartridge Having An Attachable Delivery System, now U.S. Pat. No. 6,135,771.

FIELD OF INVENTION

This invention relates to dental capsules or cartridges, and more specifically to a dental capsule or cartridge having a discharge nozzle initially sealed by a frangible break away sealing or end closure.

BACKGROUND OF THE INVENTION

In the field of dentistry, the dispensing of various dental materials, e.g. composite resin, cements, sealants and the like, directly to a tooth surface to effect a tooth restoration has been known for some time. Reference is made to the placement of such materials, e.g. filled composite resin material, directly to the site of the restoration using a syringe technique, as disclosed in U.S. Pat. Nos. 3,518,399; 3,900,954 and 4,198,756. These patents disclose the syringing technique of utilizing a capsule filled with a dental material, e.g. a composite material, from which the material was extruded by the displacement of a piston within the capsule by means of a syringe or syringe gun.

Subsequently, others have adopted the technique of syringing dental materials, such as disclosed in U.S. Pat. Nos. 4,330,280 and 4,384,853. As the syringing technique and the use of capsules for dispensing such dental materials has gained recognition as the preferred method of placing dental materials, others followed with other capsule configurations, as evidenced by U.S. Pat. Nos. 4,391,590; 4,619,613; 4,767,326; 4,963,093; 4,969,816; 5,100,320; 5,322,440 and 5,460,523, to cite a few. While the syringing technique and the use of preloaded capsules of the various known constructions proved satisfactory for the placement of various dental materials, difficulty has been encountered in effectively sealing the discharge end of the nozzle to protect the contents of the capsules from contaminants such as dirt, dust, moisture, light and/or the like.

For example, U.S. Pat. No. 3,518,399 issued to William B. Dragan disclosed an embodiment of a capsule having its discharge nozzle initially sealed during the molding of the capsule. Protecting the contents of the capsule that has its discharge nozzle initially sealed thus required a dentist to sever the sealed end with a cutting tool, e.g. a scissor or knife. However, once the sealed end was severed, it could not be readily resealed, if need be.

The other known dental capsules, as indicated in the exemplary patents cited herein, are formed with a discharge nozzle which is opened at the discharge end, and which open end is subsequently sealed with a relatively small sealing cap to protect the content of the capsule, e.g. as shown in U.S. Pat. Nos. 4,391,590; 4,963,093 and 5,100,320 to cite a few. However, the difficulty and/or disadvantages that are encountered in utilizing these small sealing caps to seal the end of a capsule's discharge nozzle are that a considerable amount of time and tedious labor is required to place such small sealing caps on the discharge end of the nozzle during the manufacture and filling of such capsule. A further disadvantage that has been noted is that frequently in the shipping and handling of such sealed capsule, there is a likelihood of the sealing cap becoming inadvertently separated from the capsule, thereby exposing the contents to contaminants such as air, dirt, dust, moisture, light and the like.

The inadvertent separation of the sealing cap from the nozzle end of the capsule is further aggravated if the sealing cap is color coded to the material placed within the capsule, and/or if the material within the capsule is light cured as disclosed in U.S. Pat. No. 4,391,590. In such an event, the dentist would be unable to know the color of the material within the capsule and/or the material, if light activated, will become prematurely cured within the capsule.

SUMMARY OF THE INVENTION

An object of this invent-on is to provide a dental capsule or cartridge with a discharge nozzle which is sealed by an integrally molded sealing cap which is constructed and arranged to be readily broken away to define the nozzle discharge orifice.

Another object is to provide a dental capsule or cartridge having a discharge nozzle sealed by an integrally formed sealing cap formed with a frangible portion whereby the sealing cap can be readily separated from the nozzle to define a discharge orifice from which the material in the capsule or cartridge may be extruded.

Still another object is to provide a dental capsule or cartridge having a discharge nozzle with art integrally molded sealing cap having a frangible portion to facilitate the removal of the sealing cap to define a discharge orifice and which end cap includes means for resealing the discharge orifice in the event it is desirable to reseal the discharge orifice.

Another object is to provide a dental capsule or cartridge having a discharge nozzle formed with an integrally formed sealing cap defining an end seal for the discharge nozzle and which capsule includes a vent adjacent the other open end of the capsule or cartridge through which the capsule or cartridge is filled with a dental material.

It is an advantage that the dental cartridge is able to be sealed by the insertion of a piston or plug without causing a build up of pressure within the capsule or cartridge.

The foregoing objects and other features and advantages are attained by a capsule or cartridge having a body portion defining a reservoir for containing a predetermined amount of material and having a discharge nozzle connected to one end of the body portion and having the opposite end open, through which the material is placed or loaded into the capsule or cartridge. In accordance with this invention, the end of the discharge nozzle is initially integrally sealed with an attached sealing cap during the molding of the capsule or cartridge. The arrangement is such that the integrally formed sealing cap is provided with a readily frangible portion whereby the sealing cap can be readily separated from the end of the discharge nozzle by breaking the sealing cap at the frangible portion to form the discharge orifice through which the contents of the capsule can be extruded or dispensed.

To facilitate filling of the capsule or cartridge with material during a filling operation, a vent is provided adjacent the open end to evacuate any air being displaced during filling. Subsequent to the filling or loading of the capsule, the open end of the capsule and associated vent are sealed by the displaceable piston when seated in the open end.

To reseal the discharge orifice subsequent to "breaking off" of the integrally formed sealing cap, the sealing cap is provided with either a cavity or a spike by which the sealing cap may be used to reseal the nozzle discharge orifice, if so desired.

IN THE DRAWINGS

FIG. 1 is a perspective view of a dental capsule or cartridge embodying the invention.

FIG. 2 is a fragmentary sectional view of the capsule of FIG. 1 illustrating a detail of construction.

FIG. 3 is a fragmentary side view of the discharge nozzle and integrally formed sealing cap.

FIG. 4 is a fragmentary exploded view illustrating the "breaking" of the sealing cap to effect the separation of the sealing cap.

FIG. 5 is a fragmentary sectional detail view of the discharge nozzle with discharge orifice formed by the separation of the sealing cap.

FIG. 6 is a fragmentary sectional view of the opened end of the capsule and sealed by a displaceable piston.

FIG. 7 is a sectional view taken along line 7—7 on FIG. 1.

FIG. 8 is a sectional view of a modified form of the invention illustrating an integrally formed sealing cap capable of being used to reseal the nozzle discharge orifice.

FIG. 9 is a fragmentary detail view of the discharge nozzle of FIG. 8 in a resealed portion.

FIG. 10 is a sectional view of another modified form of the invention.

FIG. 11 is a fragmentary detail sectional view of the discharge nozzle of FIG. 10 illustrating the frangible sealing cap in a resealing position.

DETAILED DESCRIPTION

Referring to the drawings, there is shown a dental capsule or cartridge 20 which can be suitably sized to form a single dose or multiple dose capsule or cartridge. As shown in FIG. 1, the illustrated capsule or cartridge 20 includes a body portion 21 defining a reservoir 22 for containing a dental material, e.g. composite resin, cement, sealant and the like. Connected to one end of the body portion 21 is a discharge nozzle 23. As shown, the discharge nozzle 23 tapers inwardly toward the outlet end 23A. Opposite the nozzle 23, the body portion is provided with an end opening 24 for receiving the dental material to be packaged in the body portion 21 of the capsule 20. An outwardly extending flange 24A circumscribes end opening 24 and a displaceable piston 25 is inserted into the end opening 24 for sealing the dental material within the capsule 20.

In accordance with this invention, the outlet end 23A of the nozzle 23 is initially sealed by a sealing cap 26, which is integrally formed as part of the capsule 20 during the molding thereof, as such capsules are generally molded of a suitable plastic material. The sealing cap 26 is formed with a frangible portion 26A at a point where the sealing cap 26 joins the outlet end 23A of the nozzle 23. The frangible portion 26A is defined by a reduced thickness whereby the sealing cap 26 can be readily separated or broken away by the application of a force sufficient to fracture the frangible portion 26A, as illustrated in FIG. 2. It will be noted that when the sealing cap 26 is fractured along the frangible portion 26A, a discharge orifice 27 is formed at the outlet end 23A of the nozzle 23. It will be understood that the sealing cap can be variously shaped so as to provide a finger grip whereby the fracturing force can be applied thereto. In the form of the invention shown in FIGS. 1, 2 and 4, the sealing cap 26 is in the form of a flat blade to provide ease of gripping so that with minimum force, the sealing cap 26 may be "broken" about the frangible or weakened portion 26A.

In the form described, it will be noted that the capsule is initially sealed at the discharge end of the nozzle 23. To facilitate filling of the capsule 20 with a suitable dental material, a venting groove 28 extends longitudinally of the body portion 21 adjacent the end opening 24. It will be understood that one or more venting grooves 28 are circumferentially spaced about the interior surface of the end opening 24. In the illustrated form, three such venting grooves 28 are circumferentially spaced as best seen in FIG. 7. The venting grooves 28 have a limited length as will be hereinafter described. The venting grooves 28 facilitate the filling of the capsules by permitting the air being displaced by the material being placed in the body of the capsule to be vented to atmosphere via the venting groove 28 as the outlet end of the nozzle is initially sealed by sealing cap 26.

Upon the filling of the capsule 20 with a predetermined amount of dental material, the end opening 24 is sealed closed by the insertion of the displaceable piston 25. As best seen in FIG. 6, the displaceable piston 25 is provided with a rear cylindrical portion 25A sized and shaped to seal the end opening 24 and having a predetermined length L which is rendered slightly greater than the length "l" of the venting grooves 28. The portion 25B of the piston 25 extending forwardly of the cylindrical portion 25A is formed in a shape generally complimenting the interior shape of the capsule body adjacent the discharge nozzle. The circumference of the cylindrical portion 25A of the piston is sized so as to be snugly received within the open end 24 to form a seal thereat.

As the length "L" of the piston portion 25A is greater than length "l" of the venting grooves 28, the venting grooves 28 become sealed when the piston 25 is fully seated, as best seen in FIG. 6.

FIGS. 8 and 9 illustrate another form of the invention. In this embodiment, the capsule 30 is of the "parallel wall" type, wherein the body portion 31 is cylindrical in shape and is closed at one end by either a hemispherically or conically shaped end wall 32. Angularly disposed adjacent the closed end wall 32 is a discharge nozzle 33 through which the material contained within the capsule 30 is extruded.

Opposite the closed end wall 32, the body portion is provided with an open end 34 which is circumscribed by a laterally outwardly extending flange or collar 35. Circumferentially spaced about the interior surface of the body portion 31 are one or more venting grooves 38, similar to those described and shown with respect to FIGS. 1 and 6. A displaceable piston 35 is arranged to be seated in the end opening 34 similar to that hereinbefore described.

In this form of the invention, the sealing cap 36 initially formed integral with the discharge end of nozzle 33 is illustrated in the shape of a cone. As shown, the small end of the cone shaped sealing cap 36 is initially integrally connected to the discharge end of the nozzle 33 by a frangible or weakened portion 36A, similar to that described with respect to FIGS. 1 and 6. Formed in the base or enlarged end of the cone shaped sealing cap 36 is a cavity or recess 37, which is sized and shaped to complement the outer surface of the discharge end of the nozzle 33.

In the embodiment of FIG. 8, it will be noted that the conical sealing cap 36 can be readily separated from the nozzle 33. by applying a force on the end cap 36 sufficient to cause a "break" about the weakened or frangible portion 36A, as hereinbefore described. The arrangement is such that when the sealing cap 36 has been separated, a discharge orifice 39 is formed at the discharge end of the nozzle. To effect a resealing of the discharge orifice 39, if desired, the cavity or recess 37 of the sealing cap 36 is press fitted or friction fitted to the discharge end of the nozzle 33 to seal the discharge orifice 39, as best seen in FIG. 9. In all other respects, the construction and operation of capsule 30 is similar to that hereinbefore described. Piston 35 is provided with a cylindrical portion 35A sized and shaped to seal both the open end 34 and venting grooves 38, as previously described and having its leading or forward portion 35B shaped and sized to complement the interior surface of the closed end wall 32.

FIGS. 10 and 11 illustrate another embodiment of the invention. In this form of the invention, the capsule 40 is similarly constructed to that disclosed in FIGS. 8 and 9, with the exception that the closed end wall 41 is generally conical in shape and the sealing cap 42 is provided with a sealing spike 42A which is adapted to be received within the discharge passageway 43 of the discharge nozzle 44 for resealing purposes.

As best seen in FIG. 10, the sealing cap 42 is integrally formed on the discharge end of nozzle 44 and connected thereto by a frangible or weakened portion 45, similar to that hereinbefore described. The sealing cap is also provided with a finger grip portion 42B, to which an outwardly extending sealing spike or projection 42A is connected. In this form of the invention, the sealing cap 42 is removed or separated by applying a force on the sealing cap sufficient to cause the weakened or frangible portion to break, as previously described. To reseal the discharge orifice 46, the spike 42A is inserted into passageway 43 of the discharge nozzle 44, as best seen in FIG. 11. It will be understood that the shape and size of the spike is such that it will frictionally fit and be retained within the passageway 43. In all other respects, the structure and operation of the embodiment of FIGS. 10 and 11 is similar to that hereinbefore described.

It will be understood that the shape and/or size of the capsule or cartridge can be variously formed as long as the defined shape includes a body portion forming a reservoir for containing a predetermined amount of dental material, a connected discharge nozzle and an opposite open end that is vented as herein described. Whether the capsule is sized to contain a single dose or multiple doses is not critical to the invention. The invention described herein can be applied to "bulk type" cartridges designed to contain multiple doses.

Forming the sealing cap so as to be integrally formed to the end of the nozzle in sealing relationship, as herein described, obviates the heretofore tedious and time consuming task of individually placing a tiny sealing cap on the end of the discharge nozzle to seal the same, and which for the most part constitutes a tedious and time consuming manual operation. Further, the integrally formed sealing cap, as herein described, obviates the previously noted problems of sealing caps becoming inadvertently separated from the capsule, which resulted in waste and/or contamination of the dental material disposed within the capsule or cartridge.

With the construction herein described, it will be noted that the dentist or user can effect the separation of the integrally formed sealing cap with or without the need of any type of cutting tool. The sealing cap described herein can be readily separated by simply applying a slight force sufficient to cause the frangible or weakened portion to break at the end of the nozzle and thereby expose the discharge orifice. Also, the same sealing cap may be used to effectively reseal the discharge orifice if so desired; which is especially desirable for those capsules or cartridges containing relatively large amounts of material or multiple doses.

While the present invention has been described with respect to a several embodiments, modifications and variations may be made without departing from the spirit or scope of this invention.

What is claimed is:

1. A unit dose dental capsule molded of a suitable plastic material comprising:
    a capsule body portion defining a reservoir for containing a predetermined amount of dental material,
    a discharge nozzle having a discharge orifice connected to one end of said body portion,
    said body portion having an open end opposite said discharge nozzle,
    means for sealing said discharge orifice,
    said means for sealing said discharge orifice including a sealing cap integrally formed and connected to said discharge nozzle and extending beyond said discharge nozzle,
    a frangible portion circumscribing said discharge nozzle adjacent the end thereof to facilitate the separation of said sealing cap from said discharge nozzle, said frangible portion being spaced slightly inwardly from the end of said discharge nozzle to define said discharge orifice upon the separation of said sealing cap from said discharge nozzle,
    a displaceable piston for sealing said open end of said body portion, and
    means for venting said capsule body portion,
    said venting means includes at least one groove formed within said body portion and longitudinally disposed adjacent the open end of said capsule body whereby said groove is sealed when said piston is seated to seal said end opening, said piston includes a cylindrical rear portion having an outer circumference corresponding to the internal circumference of said open end, and a connected forward portion shaped generally to conform to the internal shape of said capsule adjacent said discharge nozzle, the longitudinal length of said rear portion of said piston is slightly greater than the longitudinal length of said venting groove whereby said piston seals said venting groove when said piston is seated in said open end to seal said open end, said sealing cap is flattened to provide ease of gripping so that with a minimum of force the sealing cap may be broken at said frangible groove.

2. A dental capsule molded of a suitable plastic material comprising:

a capsule body portion defining a reservoir for containing a predetermined amount of material, a discharge nozzle having a conical outer surface converging to define a discharge orifice connected to one end of said capsule body portion, said capsule body portion having an open end opposite said discharge nozzle, a venting groove formed internally of said capsule body portion adjacent said open end and extending longitudinally inwardly thereof, a displaceable piston for sealing said open end and venting groove when said piston is fully seated, a sealing cap integrally connected to said discharge nozzle to seal said discharge orifice, a frangible groove circumscribing said discharge nozzle adjacent said sealing cap to facilitate the separation of said sealing cap from said discharge nozzle to form said discharge orifice, said sealing cap being conically shaped to define an apex end and a base end, said apex end being integrally connected to said discharge nozzle, and said base end having a conical recess formed therein, said conical recess having an inner conical surface complimenting said outer surface of said nozzle whereby said discharge orifice may be resealed by said conical recess being frictionally fitted to said discharge nozzle to seal said discharge opening subsequent to the separation of said sealing cap.

3. A dental capsule as defined in claim 2 whereby said discharge nozzle is angularly disposed relative said capsule body portion.

* * * * *